United States Patent
Wheatman

[19]

[11] Patent Number: 5,814,009
[45] Date of Patent: Sep. 29, 1998

[54] FLUID MANAGEMENT SYSTEM AND REPLACEABLE TUBING ASSEMBLY THEREFOR

[75] Inventor: Steven Wheatman, Lower Gwynedd, Pa.

[73] Assignee: Cabot Technology Corporation, Wilmington, Del.

[21] Appl. No.: 731,375

[22] Filed: Oct. 11, 1996

[51] Int. Cl.[6] .................................................. A61M 3/04
[52] U.S. Cl. ................... 604/21; 604/28; 606/96
[58] Field of Search .................. 604/21, 27–28, 604/55, 96; 606/27, 28, 96, 113, 114, 191

[56] References Cited

U.S. PATENT DOCUMENTS

| | | |
|---|---|---|
| 3,900,022 | 8/1975 | Widran . |
| 4,423,727 | 1/1984 | Widran . |
| 4,600,401 | 7/1986 | Kamen . |
| 4,604,089 | 8/1986 | Santangelo et al. . |
| 4,755,168 | 7/1988 | Romanelli et al. . |
| 4,795,424 | 1/1989 | Burner . |
| 4,820,265 | 4/1989 | DeSatnick et al. . |
| 4,863,425 | 9/1989 | Slate et al. . |
| 4,922,902 | 5/1990 | Wuchinich et al. . |
| 4,946,439 | 8/1990 | Eggers . |
| 5,125,746 | 6/1992 | Lipshitz . |
| 5,135,485 | 8/1992 | Cohen et al. . |
| 5,152,746 | 10/1992 | Atkinson et al. . |
| 5,178,606 | 1/1993 | Ognier et al. . |
| 5,242,390 | 9/1993 | Goldrath . |
| 5,320,091 | 6/1994 | Grossi et al. . |
| 5,322,506 | 6/1994 | Kullas . |
| 5,431,626 | 7/1995 | Bryant et al. . |
| 5,437,629 | 8/1995 | Goldrath . |
| 5,454,784 | 10/1995 | Atkinson et al. . |
| 5,460,490 | 10/1995 | Carr et al. . |
| 5,464,391 | 11/1995 | DeVale . |
| 5,470,312 | 11/1995 | Zanger et al. . |
| 5,472,420 | 12/1995 | Campbell . |
| 5,503,626 | 4/1996 | Goldrath . |
| 5,630,798 | 5/1997 | Beiser et al. . |
| 5,630,799 | 5/1997 | Beiser et al. . |

OTHER PUBLICATIONS

HYS–Surgimat® Irrigation Pump for Hysteroscopy, User Manual dated Nov. 1993.
Flow–Stat™ Fluid Management System Brochure (not dated).
CDIS™ Controlled Distention Irrigation System Instruction Manual dated 1990 and revised in Aug. 1991.
"Complications From Uterine Distention During Hysteroscopy," Franklin D. Loffer, *Uterine Distention*, pp. 177–185, undated.

*Primary Examiner*—William Lewis
*Attorney, Agent, or Firm*—Austin R. Miller

[57] ABSTRACT

A fluid delivery apparatus is provided for use during surgical procedures. It includes a pump, a controller connected to the pump, a fluid delivery tube, and a pressure transducer connected to a downstream portion of the fluid delivery tube. Also provided is a replaceable tubing assembly for use with the fluid delivery system.

21 Claims, 5 Drawing Sheets

FLUID MANAGEMENT SYSTEM AND REPLACEABLE TUBING ASSEMBLY THEREFOR

BACKGROUND OF THE INVENTION

This invention relates to a system and method for delivering fluid such as irrigation fluid to an operative site. In particular, it relates to a system for continuous control of fluid pressure as it is delivered to an operative site in response to an operator-selected pressure. This invention also relates to a replaceable tubing assembly for use with the fluid delivery system.

FIELD OF THE INVENTION

There has been a dramatic increase in the use of medical instruments such as endoscopes which require fluid irrigation to ensure visualization. As just one example of such procedures, it is estimated that nearly one million hysteroscopic procedures will be performed annually in the United States alone in the coming years. This is due in part to the increased use of hysteroscopic endometrial ablation and myoma resection, for example. Also, products capable of performing such procedures hysteroscopically have recently been approved or are in FDA-mandated testing.

Operative hysteroscopy uses pressurized non-saline, non-electrolyte solutions for distention of the uterus. These can be intravisated, which is undesirable. Excessive intravension can lead to electrolyte imbalance, which can lead to patient risk. Typically, a nurse is dedicated to measuring fluid deficit, which is a measure of the difference between the amount of fluid delivered to the patient and the amount of fluid recovered from the patient.

During such procedures, adequate pressure in the range of about 60 mm/Hg to about 140 mm/Hg may be required to distend the uterus for visualization, and this pressure should be maintained in spite of significant variations in flow rate.

Accordingly, there has been an ongoing need for a system that is capable of maintaining a continuous, steady flow of fluid at adequate pressure. The need for such a system is outlined in the article by Franklin D. Loffer entitled "Complications From Uterine Distention During Hysteroscopy" found in Chapter 35 of Uterine Distention.

Various attempts have been made to provide a reliable fluid delivery scheme. However, conventional systems have proven to have various disadvantages.

For example, various systems have been proposed which utilize a motor-driven peristaltic pump in an attempt to control the rate of fluid delivery. An example of such a system is provided under the trademark HYS-SURGIMAT by WOM GmbH. The HYS-SURGIMAT system uses a peristaltic pump to deliver fluid from a tube connected to a fluid supply, wherein the peristaltic pump advances the fluid to the patient. Other peristaltic systems are proposed by deSatnick et al U.S. Pat. No. 4,820,265; Ognier et al U.S. Pat. No. 5,178,606; Zanger et al U.S. Pat. No. 5,470,312; and Goldrath U.S. Pat. No. 5,503,626.

However, it has been discovered that peristaltic pumps can be disadvantageous because they tend to deliver fluid in a pulsatile stream. Also, peristaltic pumps may be limited with respect to how quickly they reduce the fluid supply, when needed.

Others have proposed systems that utilize reciprocating piston pumps to supply fluid. For example, the CDIS™ Controlled Distention Irrigation System offered by Zimmer, Inc. proposes the use of a reciprocating piston pump. In the Zimmer device, a mechanical piston drive is intended to force fluid through the tubing into the patient at a pre-determined pressure setting. Such a system is also proposed by Atkinson et al U.S. Pat. No. 5,152,746 and Atkinson et al U.S. Pat. No. 5,454,784. However, systems with reciprocating piston pumps share many of the disadvantages of peristaltic pumps in that the flow frequently has a pulsatile characteristic. Such systems also may introduce excessive noise into the operating room.

Another conventional system of pressure control is based on gravity, wherein the fluid pressure is determined by the height at which a fluid supply bag is hung. Such systems have disadvantages in that pressure cannot be accurately set because the height of the bag over the patient cannot be easily measured and the pressure at the patient varies dramatically with fluid flow rate.

Also, conventional systems have been proposed with a variety of schemes for measuring fluid pressure. However, such conventional systems have been discovered to have disadvantages.

Several conventional systems propose a monitor tube to communicate fluid pressure from a location near the operative site to the pump control. For example, the Zimmer CDIS system and the Atkinson patents propose a monitor line wherein a pressure-transmitting tube filled with fluid connects the hysteroscope to a diaphragm and a pressure-transmitting tube filled with air connects the diaphragm to the pump. Pressure is intended to be transmitted through the fluid-filled tube, across the diaphragm, and through the air-filled tube to the pump. Also, the deSatnick patent proposes a pressure-sensing line in which a diaphragm acts as a pressure transmitter and a fluid barrier. Fluid pressure is intended to be transmitted across the diaphragm and the pressure tube is intended to transmit pressure to the pump where the actual pressure measurement is performed. Such systems are disadvantageous because they can provide erroneous readings if the pressure-transmitting tubes are constricted as can occur in an operating room. Also, if the tubing is used to transfer fluid pressure, it will introduce an error in measurement due to head pressure if the diaphragm or pump is mounted at a different height than the operative site.

Other systems provide a pressure sensor at the pump housing. For example, the HYS-SURGIMAT system provided by WOM GmbH utilizes pressure sensors mounted at the pump housing. However, such a device must be maintained on the same level as the hysteroscope during a hysteroscopic procedure. A difference in height would influence the pressure measurement because of hydrostatic pressure.

Other systems have proposed the use of a pressure sensor mounted within the instrument itself. For example, U.S. Pat. No. 4,423,727 to Windran proposes a pressure sensor mounted within an endoscope sheath. A control circuit is intended to deactivate a fluid pump when the pressure sensed exceeds a pre-determined value, thereby stopping fluid flow. Such systems do not lend themselves to the use of disposable components. Replacement of such an internally-mounted pressure sensor in a reusable scope is labor-intensive.

Accordingly, there remains a need for a fluid delivery system adapted for use during procedures such as hysteroscopic procedures that is capable of delivering fluid safely and efficiently.

OBJECTS OF THE INVENTION

It is an object of this invention to provide a fluid delivery system and tubing assembly that overcomes the disadvantages of the prior art systems.

It is another object of this invention to provide a fluid delivery system for steady and continuous fluid flow at physician-selected pressures.

It is yet another object of this invention to provide a tubing assembly that is both inexpensive and accurate.

Other objects are apparent in view of the following description, the drawings and the appended claims.

SUMMARY OF THE INVENTION

A fluid delivery apparatus is provided for use during surgical procedures wherein fluid is delivered to a surgical site through a surgical instrument, wherein the apparatus is adapted to deliver fluid to an inlet port on the surgical instrument at an operator-selected pressure. The apparatus includes a pump for delivering fluid from a supply. The apparatus is adapted to increase, decrease or maintain the fluid supply pressure responsive to the operator-selected pressure. A fluid delivery tube is connected to the fluid supply and the surgical instrument. Fluid is thereby deliverable from the fluid supply, through the delivery tube, and into the surgical instrument under the influence of the pump. The fluid delivery apparatus is also provided with a pressure transducer that is connected to the downstream portion of the fluid delivery tube so that it can be positioned adjacent to the instrument. In operation, the system is adapted to increase, decrease or maintain a substantially constant fluid pressure in response to the pressure transducer and the operator-selected pressure. A replaceable tubing assembly and a method are also provided.

DETAILED DESCRIPTION OF THE INVENTION

Figure 1:
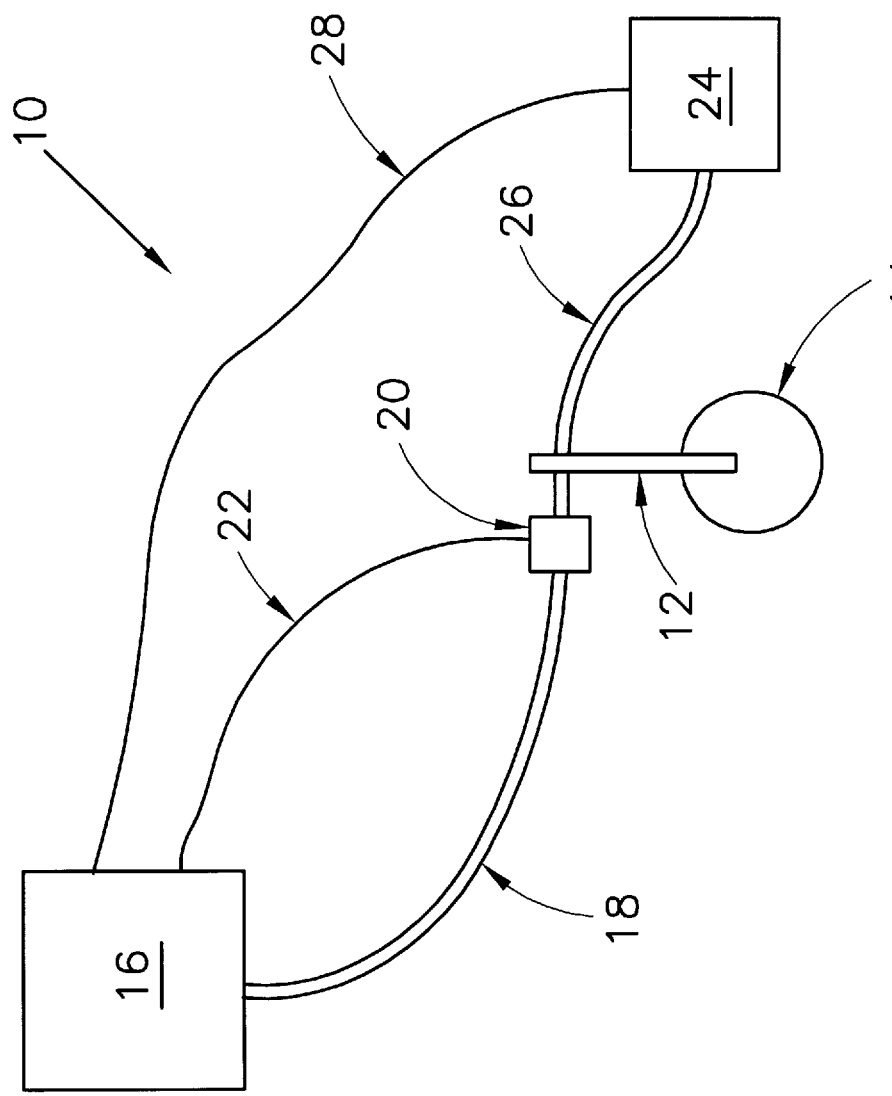
FIG. 1 is a schematic representation of an embodiment of a fluid management system according to this invention.

The following description is intended to refer to the specific embodiments of the invention illustrated in the drawings. This description is not intended to define or limit the scope of the invention, which is defined separately in the claims that follow.

Although it is contemplated for use with a variety of procedures, the fluid management system according to this invention, and the replaceable tubing assembly and method therefor, is described with reference to hysteroscopy procedures.

The system according to this invention preferably comprises a pump, including hardware and software, and a consumable tubing set or assembly. The pump is preferably a stand-alone unit which houses a bag of sterile water, mannitol or sorbitol, for example. The replaceable tubing set is used to deliver fluid from the pump to the inflow port on a resectoscope, for example.

The preferred fluid management system receives three inputs of information. A pressure sensor built into the tubing measures the pressure of the fluid at a location adjacent to the instrument input and triggers the electronic control system to increase, decrease or maintain the fluid pressure. The user can set a desired driving pressure, preferably between about 40 and about 140 mm/Hg. A control panel allows the user to set the desired pressure.

A cradle load cell assembly is preferably provided to weigh the fluid supply and a base load cell assembly is preferably provided to weight a fluid collection canister. Accordingly, the cradle load cell preferably determines the amount of fluid infused, and the base load cell preferably determines the amount of fluid collected. The fluid management system then calculates a fluid deficit.

The fluid management system according to this invention is preferably adapted to provide liquid distention of the uterus for operative hysteroscopy. Although intrauterine distention can usually be accomplished with pressures in the range of about 35 to about 75 mm/Hg, the system preferably provides a range up to about 140 mm/Hg.

Referring now to FIG. 1, a schematic representation of a preferred fluid management system is generally designated by the numeral "10". System 10 is adapted for use with a medical instrument 12 such as a hysteroscope. Instrument 12 is inserted, during an operative procedure, into an operative site 14 such as a uterus.

A pneumatic pump 16 is provided to deliver fluid at an operator-selected pressure for irrigation of operative site 14. The housing for pump 16 preferably encloses a bladder-type pump, a control system, an air compressor, a cradle load cell and other pump components, as will be described later. A fluid delivery tube assembly 18 is provided between pump 16 and an inlet of instrument 12. Tube assembly 18 includes a pressure transducer 20 that is positioned at a downstream portion of the tubing and is positioned adjacent to, and external of, the inlet port to instrument 12. Fluid delivery tube assembly 18 also includes an electrical cable 22 for transmitting electrical signals from pressure transducer 20 to pneumatic pump 16 for control of the pump and fluid pressure.

Fluid management system 10 preferably includes a fluid collection assembly including a fluid canister and a base load cell. Collection assembly 24 receives irrigation fluid from operative site 14 by means of a fluid collection tube 26 or other known means. Collection assembly 24 is connected to pneumatic pump 16 by means of an electrical cable 28 which transmits a signal corresponding to collected fluid weight. The preferred collection assembly includes a drape, drape tubing, collection canister, and a vacuum line connected between the collection canister and a vacuum connection port.

Pneumatic pump 16 controls fluid pressure in response to an operator-selected pressure and the signal from pressure transducer 20. Also, pump 16 preferably calculates a fluid deficit in terms of volume by comparison between the weight signal from collection assembly 24 and the weight signal from a cradle load cell within pump 16.

The preferred system includes two load cells; an upper or cradle load cell for measuring the weight of a fluid supply bag, and a lower or base load cell for measuring the weight of a collection canister.

The preferred system also includes two pressure transducers; a transducer mounted on the fluid delivery tube to measure the fluid pressure, and a transducer mounted in the pump to measure air pressure in the bladder or pressure chamber, if required.

Figure 2:
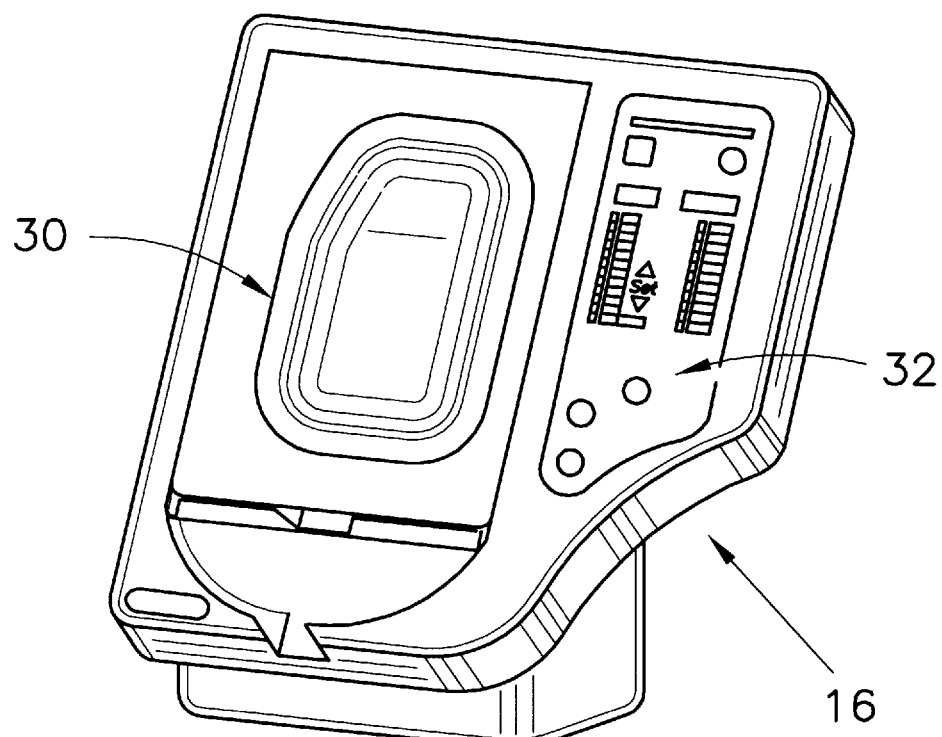
FIG. 2 is a perspective view of a pump that can be used in the fluid management system shown in FIG. 1.
Figure 2:
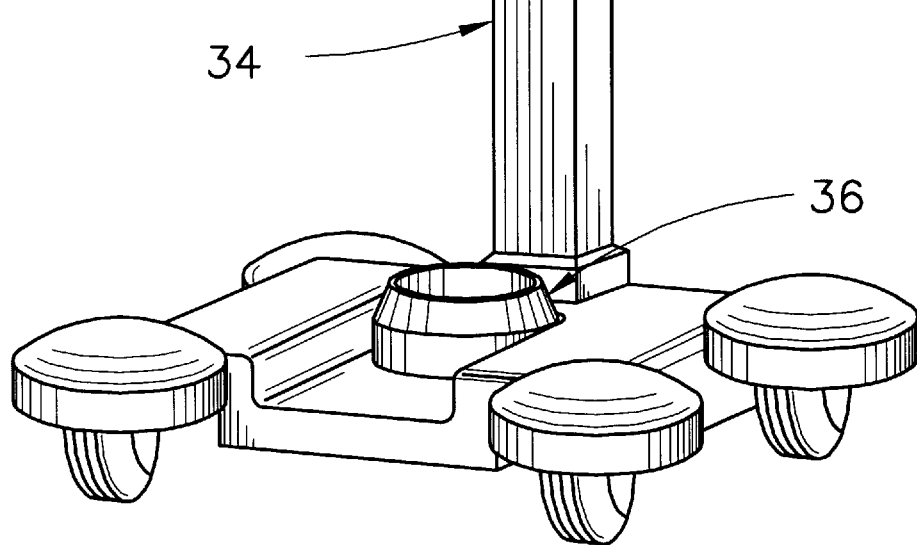

Referring now to FIG. 2, details of one embodiment of a pneumatic pump 16 are illustrated. Pump 16 is preferably provided with a bladder-type pump 30. Details of such a pump are provided in co-pending application Ser. No. 08/680,108, filed Jul. 15, 1996. The preferred pump includes a bladder for inflation by air, an air compressor, solenoid valves to direct air from the compressor from the atmosphere to the bladder or from the bladder to the atmosphere, an overpressure switch to remove power from the compressor, and a mechanical overpressure relief valve. Most preferably, pump 30 utilizes a compressor (such as Model No. AC0502-A1017-D1-0511 provided by Medo USA) to provide pressurized air to inflate a bladder that is positioned adjacent to a fluid bag. As the bladder is inflated, it exerts a force against the fluid bag and causes the fluid to be expelled from the bag at a selected pressure. Although not shown in FIG. 2, a tubing assembly is connected to the fluid supply for delivery of the fluid from the fluid bag and to the surgical instrument.

Figure 3:
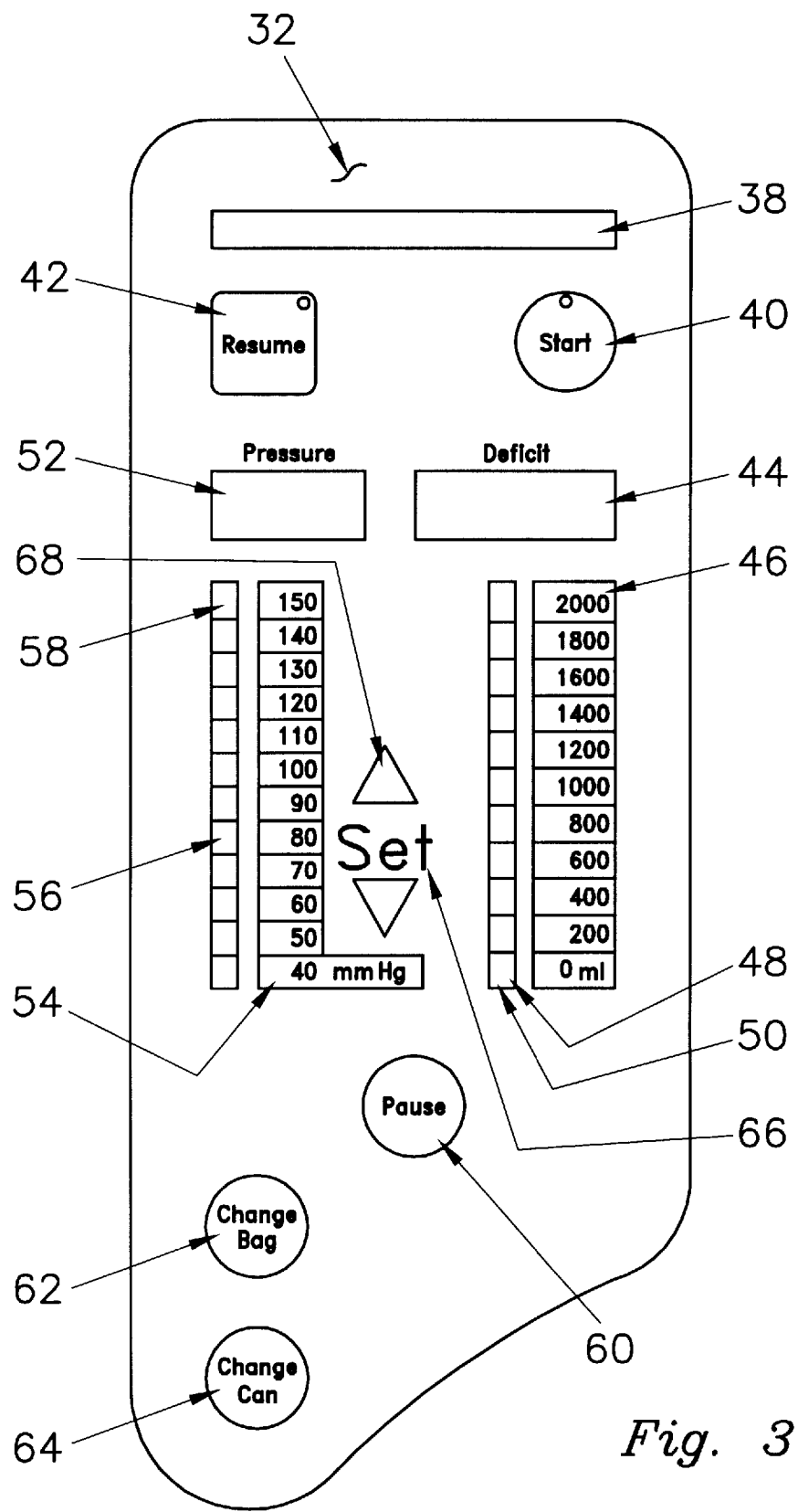
FIG. 3 illustrates an embodiment of a control panel adapted for use with the pump shown in FIG. 2.

Pneumatic pump 16 also includes a control panel 32, details of which are illustrated in FIG. 3. Pump 30 of pneumatic pump 16 is mounted on a stand 34 which is connected to a base 36. Base 36 is adapted to support a fluid collection assembly such as assembly 24 shown schematically in FIG. 1.

Referring now to FIG. 3, a preferred control panel 32 is illustrated. Panel 32 includes a message display 38 which uses a digital display to relay messages to the system operator. For example, the message "BAG CHANGE" may be provided when the weight signal from the cradle load cell indicates that the bag is nearly empty. Also, the message "CONNECT TRANSDUCER TO IN-FLOW & CABLE" may be displayed to indicate a set-up action to be taken.

Control panel 32 also includes a start button 40 which can be pressed to initiate operation of the system. A resume button 42 is used to continue pump operation after the system is paused or during various start-up procedures. Digital deficit volume display 44 provides a digital indication of fluid deficit. A deficit volume level 46 is also provided and includes a visual deficit volume indicator 48 with a plurality of LEDs 50.

A digital pressure display 52 is provided to indicate measured pressure. Also provided is a pressure level 54 with a visual pressure indicator 56 with a plurality of LEDs 58.

Accordingly, both fluid pressure and fluid deficit are preferably indicated digitally and graphically. A pause button 60 can be depressed to pause the pump, and a change bag button 62 can be pressed to allow the user to change to a new fluid bag of distention media (the pump deflates the bladder so that the user can open the door latch and change the bag). The change can button 64 is pressed to allow the user to change the collection canister.

Control panel 32 is provided with a set point adjustment 66 with a set point display 68. Set point adjustment 66 is used by an operator of the system to adjust and select the desired distention pressure.

Figure 4:
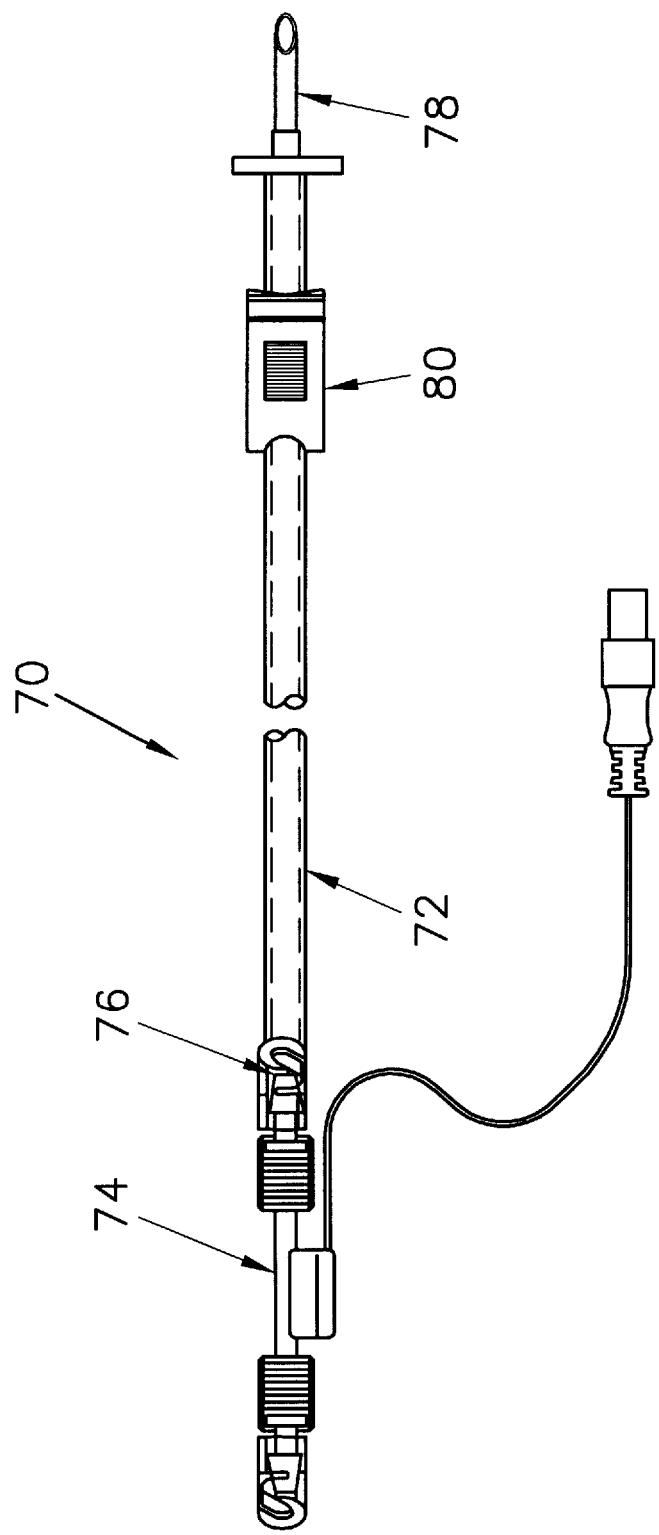
FIG. 4 illustrates an embodiment of a replaceable tubing assembly according to this invention.

Referring now to FIG. 4, a preferred embodiment of a replaceable tubing assembly is generally designated by the numeral "70". The tubing assembly 70 is an inexpensive, disposable product that is adapted for efficient use with the reusable pump assembly. The replaceable tubing assembly 70 is important to the fluid management system because it provides a passage through which fluid is delivered from the pump to the medical instrument. It also provides means with which pressure of distention fluid is measured. The tubing assembly is replaceable so that there is no need to clean delivery tubing and, more importantly, any damage to the pressure transducer that could occur during an operative procedure will not carry over to a subsequent procedure.

Tubing assembly 70 includes a delivery tube 72 that is preferably flexible and long enough to comfortably reach from the pump housing to a position adjacent to the medical instrument inlet port. Tubing assembly 70 also includes a pressure transducer assembly 74, details of which will be described with reference to FIG. 5. Delivery tube 72 is connected to pressure transducer assembly 74 by means of a standard leur connection 76. Such a connection provides for fluid flow between the downstream end of delivery tube 72 and the upstream end of pressure transducer assembly 74. At the upstream end of delivery tube 72 are provided a spike 78 for releasable connection to a fluid bag and a clamp 80 for permitting or preventing fluid flow through delivery tube 72.

Tubing assembly 70 is preferably provided in a sterile package for connection to the fluid management system just before an operative procedure. Alternatively, pressure transducer assembly 74 is provided in such a sterile kit if it is convenient for the operator to provide a delivery tube 72 with a leur connection 76 for mating to the pressure transducer assembly 74.

Figure 5:
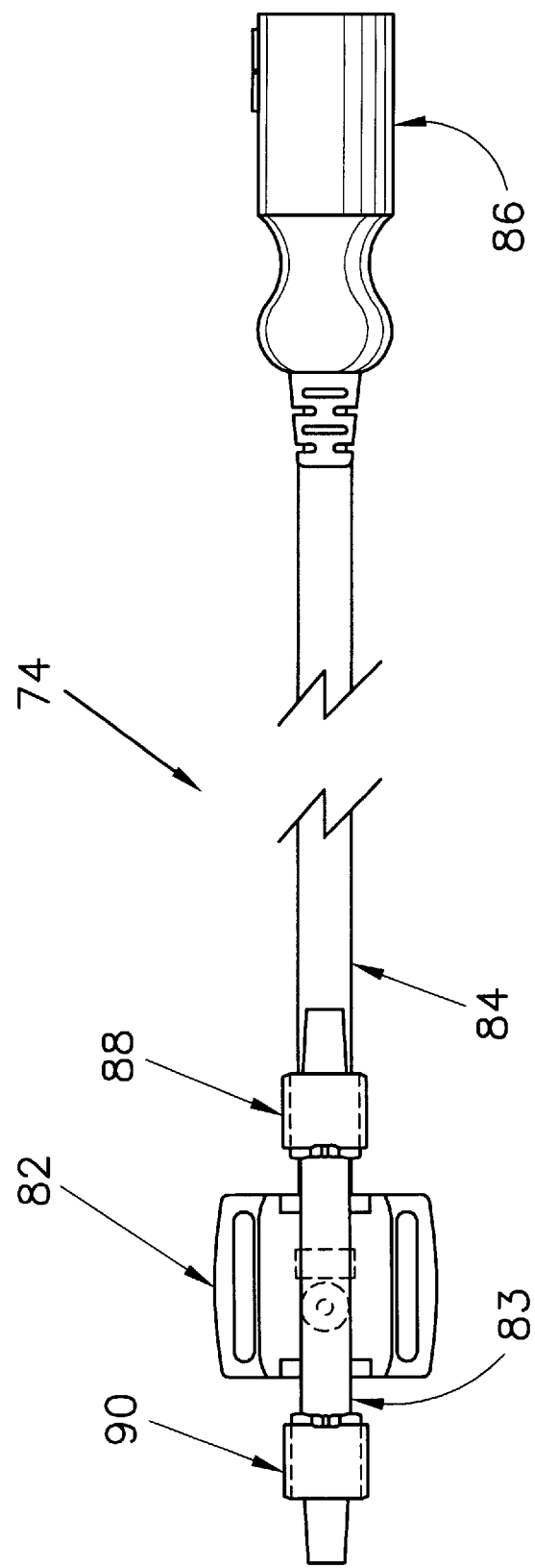
FIG. 5 illustrates an embodiment of a pressure transducer assembly adapted for use with the replaceable tubing assembly illustrated in FIG. 4.

Referring now to FIG. 5, details of pressure transducer assembly 74 will now be described. Transducer assembly 74 includes a transducer body 82 that is preferably connected to a rigid tube 83 provided with leur connectors 88 and 90 mounted at either end—at an upstream end of rigid tube 83 for connection to delivery tube 72 (FIG. 4) and at a downstream end for connection to the inlet port of a surgical instrument (not shown). Connected to transducer body 82 is an electrical cable 84 that terminates at an electrical connector 86. Electrical connector 86 is adapted for connection to provide an electrical signal corresponding to pressure to the pump. Electrical cable 84 is preferably selected so that it can withstand the forces and manipulation generally encountered in an active operating room. Most preferably, it will be capable of withstanding bending and squeezing without compromising the signal from the pressure sensor to the pump controller.

Transducer body 82 includes a pressure sensor, a converter for converting the sensed pressure into an electrical signal such as an output voltage, and means for transmitting the signal from the converter to the pump controller. It has been discovered that transducers traditionally designed for physiological pressure measurement and invasive pressure monitoring can be adapted for use with pressure transducer assembly 74. One such transducer is sold under Model No. 041-590-505 provided by Cobe Patient Monitoring Products.

Transducer body 82 preferably includes an electronic chip. The chip is preferably mounted within a plastic sensor housing. A gel is preferably provided to communicate the pressure wave from the fluid pathway through an opening in a ceramic carrier to a diaphragm.

A sealing O-ring is attached to a chip carrier and isolation gel is placed in the cavity to communicate the pressure wave (as described above) and to isolate the silicon die from fluid in the pathway and to insulate the die from outside electrical interference.

The plastic sensor housing of transducer body 82 preferably comprises upper and lower bodies. The upper body is molded in a single piece to avoid leakage. The lower body is molded. The components are assembled to produce a transducer body assembly that is inexpensive and accurate.

Operation of the fluid management system according to this invention will now be described with general reference to FIGS. 1–5. An operator of fluid manage system 10 will select a pressure using set point adjustment 66 on control panel 32 (FIG. 3). As fluid is delivered from pneumatic pump 16 by means of bladder-type pump 30, pressure of the delivered fluid is measured at a position proximal to the medical instrument 12 and operative site 14 by means of pressure transducer 20 (FIG. 1). The controller in pneumatic pump 16 will adjust the air pressure in the pump bladder in order to increase, decrease, or to substantially maintain the fluid pressure in response to the operator-selected pressure as well as the sensed pressure. A closed-loop, continuous control of fluid pressure is maintained by pneumatic pump 16. A steady and continuous stream of irrigation fluid is thereby provided to the patient without pulsations in the fluid stream and with quick response to changes in the system conditions throughout the operative procedure.

The control system preferably operates with respect to the following variable pressures: the set pressure desired in the tubing adjacent to the instrument, as selected by the user; the actual pressure existing adjacent to the instrument based on voltage output from the transducer; and the internal pressure of the bladder pump or pressure chamber.

In operation, if the actual pressure exceeds the set pressure by a predetermined amount, then the controller shall cause the bladder to be deflated until actual pressure is within a preset range. This is performed by opening a vent valve or by using the compressor and valves to remove air from the bladder. If actual pressure is below set pressure by more than a predetermined amount, then the software and controller will cause the bladder to be inflated until the actual pressure comes within a preset range. This is performed by actuation of the air compressor and valves to introduce air into the bladder. If actual pressure is within a preset range, then the software optionally causes the air compressor and valves to bring actual pressure closer to the set pressure.

In steady-state operation, the actual pressure is preferably maintained within 5 mm/Hg of the set pressure. Alarms are preferably provided when the difference between actual and set pressures exceeds 10 mm/Hg or when the actual pressure exceeds 165 mm/Hg.

The volumetric deficit of fluid is calculated and reported to the operator based on a comparison between the weight signal from the base load cell and the weight signal from the cradle load cell. Appropriate alarms are actuated when the volume deficit exceeds a pre-determined safe level.

Many modifications can be made to the embodiments selected for illustration in the drawings without departing from the spirit or the scope of this invention, which is defined separately in the claims that follow. Although the invention is described with reference to hysteroscopic procedures and hysteroscopes, it is contemplated that the fluid management system and replaceable tubing assembly according to his invention can be used for a wide variety of procedures.

In any embodiment, a fluid management system according to this invention controls and monitors the pressure of fluid such as distention fluid as it is supplied to a surgical instrument such as a hysteroscope. The system is capable of providing dynamic pressure control adjacent the instrument to compensate for any pressure loss in the delivery tubes.

What is claimed is:

1. A replaceable tubing assembly for use with a fluid delivery system having a pump for delivering fluid at an operator-selected pressure from a supply, a surgical instrument through which fluid is delivered to a surgical site, and a controller connected to said pump, said controller being responsive to said operator-selected pressure, said replaceable tubing assembly comprising:

a fluid delivery tube defining a passage for the flow of fluid, said fluid delivery tube comprising an upstream portion for releasable connection to the supply of fluid and a downstream portion with a downstream end positioned for releasable connection to the surgical instrument, whereby fluid is deliverable from the supply of fluid, through said passage, and into the surgical instrument under the influence of the pump; and a pressure transducer connected to said fluid delivery tube at said downstream portion, said pressure transducer positioned to sense the pressure of fluid in said passage in said downstream portion of said fluid delivery tube for generating an electrical signal corresponding to sensed fluid pressure, and means connected to said pressure transducer and adapted for releasable connection to the controller for transmitting said electrical signal from said pressure transducer to the controller;

wherein, during use, said upstream portion of said fluid delivery tube is releasably connected to the supply of fluid, said downstream end of said fluid delivery tube is releasably connected to the surgical instrument, and said means for transmitting said electrical signal is releasably connected to the controller, and wherein fluid pressure in said downstream portion of said fluid delivery tube is continuously controlled by said controller to increase, decrease or maintain a substantially constant fluid pressure in response to said electrical signal from said pressure transducer and the operator-selected pressure.

2. A replaceable tubing assembly for use with a fluid delivery system having a pump for delivering fluid at an operator-selected pressure from a supply, a surgical instrument having an inlet port through which fluid is delivered to a surgical site, and a controller connected to said pump, said controller being responsive to said operator-selected pressure, said replaceable tubing assembly comprising:

a fluid delivery tube comprising an upstream portion with an upstream connector positioned for releasable connection to the supply of fluid and a downstream portion with a downstream connector positioned for releasable connection to the inlet port on the surgical instrument, whereby fluid is deliverable from the supply of fluid, through said fluid delivery tube, and into the inlet port on the surgical instrument under the influence of the pump, wherein said fluid delivery tube receives fluid from the pump under the influence of pneumatic pressure; and a pressure transducer connected to said downstream portion of said fluid delivery tube proximal to said downstream connector, said pressure transducer comprising a pressure sensor positioned to sense fluid pressure in said downstream portion of said fluid delivery tube, a converter connected to said pressure sensor for generating an electrical signal corresponding to sensed fluid pressure, and means connected to said converter and adapted for releasable connection to the controller for transmitting said electrical signal from said pressure transducer to the controller;

wherein, during use, said upstream connector of said fluid delivery tube is releasably connected to the supply of fluid, said downstream connector of said fluid delivery tube is releasably connected to the inlet port on the surgical instrument, and said means for transmitting said electrical signal is connected to the controller, and wherein fluid pressure in said downstream portion of said fluid delivery tube is continuously controlled by said controller to increase, decrease or maintain a substantially constant fluid pressure in response to said electrical signal from said pressure transducer and the operator-selected pressure.

3. The replaceable tubing assembly defined in claim 2, wherein said means for transmitting said electrical signal comprises an electrical cable extending from a position adjacent to said converter to an electrical connector adapted for releasable electrical connection to the controller.

4. The releasable tubing assembly defined in claim 2, wherein said pressure sensor comprises a diaphragm positioned for response to said fluid pressure in said downstream portion of said fluid delivery tube.

5. The releasable tubing assembly defined in claim 2, wherein said converter comprises an electrical circuit for generating an excitation voltage.

6. The releasable tubing assembly defined in claim 2, wherein said downstream portion of said fluid delivery tube comprises a rigid tube section with a connector at its downstream end for connection adjacent to the inlet port on the surgical instrument.

7. A fluid delivery apparatus for use during surgical procedures wherein fluid is delivered to a surgical site through a surgical instrument, said fluid delivery apparatus being adapted to deliver fluid to the surgical instrument at an operator-selected pressure, said fluid delivery apparatus comprising:

a pump positionable upstream from said surgical instrument for delivering fluid from a supply;

a controller connected to said pump for substantially continuous control of said pump to increase, decrease or maintain the pressure of fluid as it is delivered by said pump toward said surgical instrument downstream of said pump, said controller being responsive to said operator-selected pressure;

a fluid delivery tube comprising an upstream portion for connection to the supply of fluid and a downstream portion for connection to the surgical instrument, whereby fluid is deliverable from the supply of fluid, through said fluid delivery tube, and into the surgical instrument under the influence of said pump; and a pressure transducer connected to said downstream portion of said fluid delivery tube for positioning adjacent to the surgical instrument, said pressure transducer positioned to sense fluid pressure in said downstream portion of said fluid delivery tube for generating an electrical signal corresponding to sensed fluid pressure, and means for electrically connecting said pressure transducer to said controller for transmitting said electrical signal from said pressure transducer to said controller;

whereby said controller substantially continuously controls said pump to increase, decrease or maintain a substantially constant pressure under which fluid is delivered through said fluid delivery tube to the surgical instrument in response to a comparison between said electrical signal from said pressure transducer and said operator-selected pressure.

8. A fluid delivery apparatus for use during surgical procedures wherein fluid is delivered to a surgical site through a surgical instrument said fluid delivery apparatus being adapted to deliver fluid to an inlet port on the surgical instrument at an operator-selected pressure said fluid delivery apparatus comprising:

a pump positioned for delivering fluid from a supply, wherein said pump is a pneumatic pump for delivering fluid under the influence of pneumatic pressure, wherein said pneumatic pump is positioned for applying a force to the supply of fluid;

a controller connected to said pump to increase, decrease or maintain the pressure at which fluid is delivered by said pump, said controller being responsive to said operator-selected pressure:

a fluid delivery tube comprising an upstream portion for connection to the supply of fluid and a downstream portion for connection to the inlet port on the surgical instrument, whereby fluid is deliverable from the supply of fluid, through said fluid delivery tube, and into the inlet port on the surgical instrument under the influence of said pump; and a pressure transducer connected to said downstream portion of said fluid delivery tube for positioning adjacent to the inlet port on the surgical instrument, said pressure transducer comprising a pressure sensor positioned to sense fluid pressure in said downstream portion of said fluid delivery tube, a converter connected to said pressure sensor for generating an electrical signal corresponding to sensed fluid pressure, and means for electrically connecting said pressure transducer to said controller for transmitting said electrical signal from said pressure transducer to said controller, whereby said controller substantially continuously controls said pump to increase, decrease or maintain a substantially constant pressure under which fluid is delivered through said fluid delivery tube in response to said electrical signal from said pressure transducer and said operator-selected pressure.

9. The fluid delivery apparatus defined in claim 8, wherein said pneumatic pump comprises a bladder positioned to contact the supply of fluid, wherein inflation of said bladder exerts a force against the supply of fluid to deliver fluid therefrom.

10. The fluid delivery apparatus defined in claim 8, wherein said pneumatic pump comprises a pressure chamber within which the supply of fluid is positioned, wherein pressurization of said pressure chamber exerts a force against the supply of fluid to deliver fluid therefrom.

11. The fluid delivery apparatus defined in claim 8, further comprising means for measuring a quantity of fluid delivered from the supply and means for measuring a quantity of fluid collected from a surgical patient.

12. The fluid delivery apparatus defined in claim 11, wherein said means for measuring fluid delivered and said means for measuring fluid collected each comprises a load cell.

13. The fluid delivery apparatus defined in claim 11, further comprising means for comparing said quantity of fluid delivered with said quantity of fluid collected, means for calculating volumetric fluid deficit, and a display of said fluid deficit.

14. A method of delivering fluid from a fluid supply in a pump housing and into a surgical instrument for irrigation of a surgical site, said method comprising the steps of:

(a) exerting a force against said fluid supply in response to an operator-selected pressure, thereby forcing fluid to exit said fluid supply under the influence of said force;

(b) delivering fluid from said fluid supply to an inlet port on said surgical instrument through a tube connected to said fluid supply at its upstream end and connected to said inlet port at its downstream end;

(c) sensing pressure of fluid at a downstream portion of said tube at a position adjacent to said inlet port;

(d) converting sensed pressure to an electrical signal at a downstream portion of said tube at a position adjacent to said inlet port;

(e) transmitting said electrical signal from said downstream portion of said tube to a controller connected to said pump housing; and (f) controlling said force against said fluid supply in response to said operator-selected pressure and said electrical signal from said downstream portion of said tube, thereby delivering fluid from said fluid supply to said surgical instrument under steady and continuous control with substantially continuous adjustments to said force in order to maintain said operator-selected pressure.

15. The method defined in claim 14, further comprising the steps of:

(a) measuring the quantity of fluid delivered from said fluid supply;

(b) measuring the quantity of fluid collected from said surgical site;

(c) calculating any fluid deficit by comparing the quantity of fluid delivered with the quantity of fluid collected; and (d) displaying said fluid deficit.

16. The method defined in claim 14, wherein said exerting step comprises generating a pneumatic pressure adjacent to said fluid supply in response to said operator-selected pressure.

17. The method defined in claim 14, wherein said sensing step comprises positioning a diaphragm at a downstream portion of said tube for response to said pressure of said fluid at a downstream portion of said tube.

18. The method defined in claim 14, wherein said controlling step comprises continuous, closed-loop control of said force exerted against said fluid supply in response to said electrical signal from said downstream portion of said tube, thereby increasing, decreasing or maintaining said force to provide a downstream fluid pressure substantially corresponding to said operator-selected pressure.

19. A replaceable tubing assembly for use with a fluid delivery system having a pump for delivering fluid at an operator-selected pressure from a supply, a surgical instrument having an inlet port through which fluid is delivered to a surgical site, and a controller connected to said pump, said controller being responsive to said operator-selected pressure, said replaceable tubing assembly comprising:

a fluid delivery tube comprising an upstream portion with an upstream connector positioned for releasable connection to the supply of fluid and a downstream tubing portion with a downstream connector positioned for releasable connection to the inlet port on the surgical instrument, whereby fluid is deliverable from the supply of fluid, through said fluid delivery tube, and into the inlet port on the surgical instrument under the influence of the pump, wherein said fluid delivery tube receives fluid from the pump under the influence of pneumatic pressure; and a pressure transducer mounted to the wall of said downstream tubing portion of said fluid delivery tube proximal to said downstream connector at a location that is upstream of said downstream connector, said pressure transducer comprising a pressure sensor positioned to sense fluid pressure in said downstream tubing portion of said fluid delivery tube, a converter connected to said pressure sensor for generating an electrical signal corresponding to sensed fluid pressure, and means connected to said converter and adapted for releasable connection to the controller for transmitting said electrical signal from said pressure transducer to the controller;

wherein, during use, said upstream connector of said fluid delivery tube is releasably connected to the supply of fluid, said downstream connector of said fluid delivery tube is releasably connected to the inlet port on the surgical instrument, and said means for transmitting said electrical signal is connected to the controller, and wherein fluid pressure in said downstream tubing portion of said fluid delivery tube is continuously controlled by said controller to increase, decrease or maintain a substantially constant fluid pressure in response to said electrical signal from said pressure transducer and the operator-selected pressure.

20. A fluid delivery apparatus for use during surgical procedures wherein fluid is delivered from a fluid supply and to a surgical site through a surgical instrument, said fluid delivery apparatus being adapted to deliver fluid to an inlet port on the surgical instrument at an operator-selected pressure, said fluid delivery apparatus comprising:

a pump positioned for delivering fluid from a supply in a substantially continuous and steady flow, wherein said pump is a pneumatic pump for delivering fluid from said fluid supply under the influence of pneumatic pressure, wherein said pneumatic pump is positioned for applying a force to said fluid supply to expel fluid from said fluid supply;

a controller connected to said pump to increase, decrease or maintain the pressure at which fluid is delivered by said pump, said controller being responsive to said operator-selected pressure;

a fluid delivery tube comprising an upstream portion for connection to said fluid supply and a downstream portion for connection to the inlet port on the surgical instrument, whereby fluid is deliverable from said fluid supply, through said fluid delivery tube, and into the inlet port on the surgical instrument under the influence of said pump; and a pressure transducer connected to said downstream portion of said fluid delivery tube for positioning adjacent to the inlet port on the surgical instrument, said pressure transducer comprising a pressure sensor positioned to sense fluid pressure in said downstream portion of said fluid delivery tube, a converter connected to said pressure sensor for generating an electrical signal corresponding to sensed fluid pressure, and means for electrically connecting said pressure transducer to said controller for transmitting said electrical signal from said pressure transducer to said controller;

whereby said controller substantially continuously controls said pump to increase, decrease or maintain a substantially constant pressure under which fluid is delivered through said fluid delivery tube in response to said electrical signal from said pressure transducer and said operator-selected pressure.

21. The replaceable tubing assembly defined in claim 20, wherein said pressure transducer is mounted to said fluid delivery tube at a location that is upstream of a downstream end thereof.

* * * * *